United States Patent [19]

Taylor

[11] Patent Number: 5,709,693
[45] Date of Patent: Jan. 20, 1998

US005709693A

[54] STITCHER

[75] Inventor: Charles Taylor, San Francisco, Calif.

[73] Assignee: Cardiothoracic System, Inc., Cupertino, Calif.

[21] Appl. No.: 650,153

[22] Filed: Feb. 20, 1996

[51] Int. Cl.[6] ................................................. A61B 17/04
[52] U.S. Cl. ......................... 606/145; 606/144; 606/139
[58] Field of Search ................................. 606/144, 139, 606/145, 147, 148; 112/169

[56] References Cited

U.S. PATENT DOCUMENTS

| | | |
|---|---|---|
| 1,822,330 | 9/1931 | Ainslie . |
| 4,027,608 | 6/1977 | Arbuckle . |
| 4,109,658 | 8/1978 | Hughes . |
| 4,235,177 | 11/1980 | Arbuckle . |
| 4,345,601 | 8/1982 | Fukuda . |
| 4,557,265 | 12/1985 | Andersson ........................... 128/340 |
| 4,899,746 | 2/1990 | Brunk ................................. 606/144 |
| 5,306,281 | 4/1994 | Beurrier ............................. 606/144 |
| 5,308,353 | 5/1994 | Beurrier ............................. 606/144 |
| 5,437,681 | 8/1995 | Meade et al. . |

*Primary Examiner*—Michael Buiz
*Assistant Examiner*—Tina T. D. Pham
*Attorney, Agent, or Firm*—Lyon & Lyon LLP

[57] ABSTRACT

An automated stitching device having a "C"-shaped arcuate needle which is incrementally advanced in a circular path. A toggle and drive plate arrangement is used to drive the needle, and a one-way clutch mechanism is used to engage and permit incremental advancement of the needle along its circular path. The "C"-shaped arcuate needle is mounted and driven at the distal end of an elongated shaft. The stitching device is particularly suited for microsurgery, laparoscopic surgery, and various less invasive surgical procedures, and particularly for the suturing of blood vessels including during cardiac bypass surgery.

6 Claims, 3 Drawing Sheets

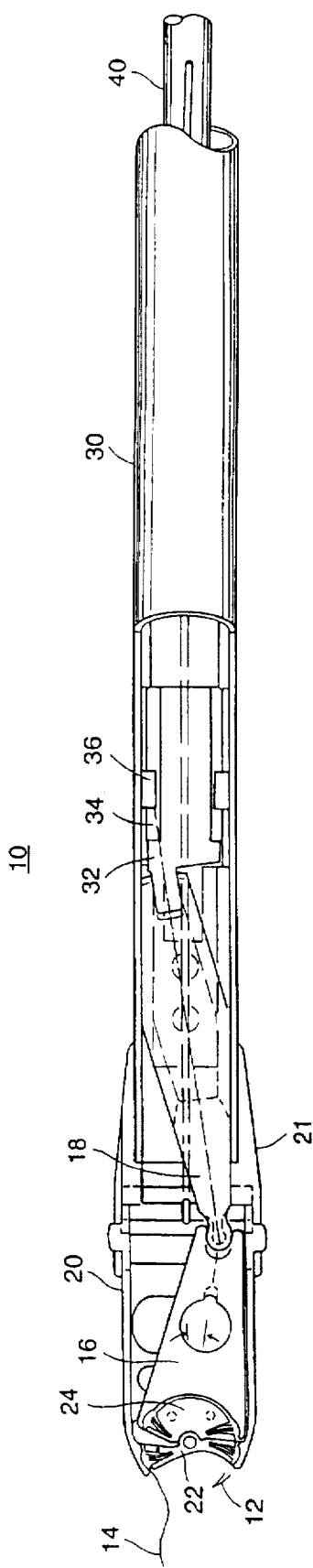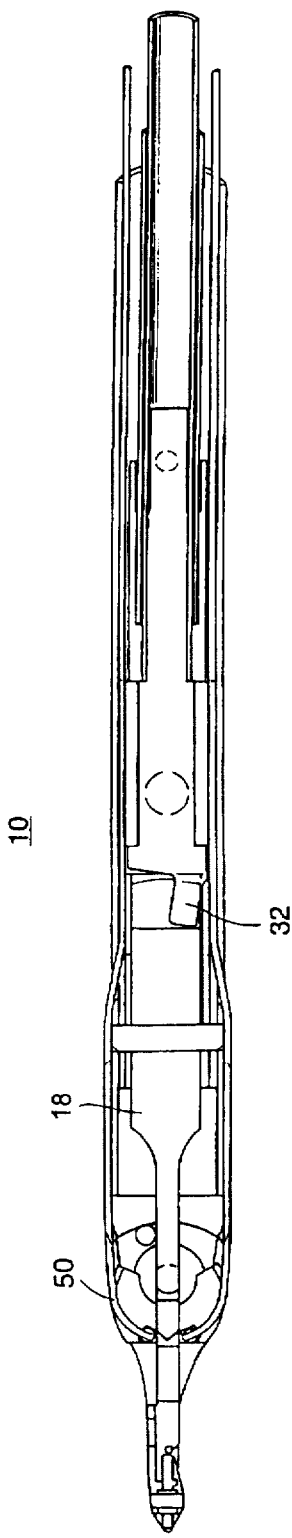

STITCHER

BACKGROUND OF THE INVENTION

This invention relates generally to an automated stitching or suturing device. More particularly, this invention relates to an automated stitching or suturing device which can be used advantageously in surgical procedures such as coronary by-pass surgery, laparoscopic procedures, and various less invasive surgical procedures.

Suturing by surgeons is currently generally accomplished by manual suturing of tissues, whereby the surgeon uses a fine pair of pliers to grab and hold a suture needle, pierce the tissue with the needle, let go of the needle, and regrab the needle to pull the needle and accompanying suture thread through the tissues to be sutured. Such needles may be curved or "C"-shaped, with the suture thread attached to the back end of the needle.

Automated suturing devices, including devices described as suitable for microsurgery, are known. For example, U.S. Pat. No. 4,557,265 to Andersson describes a suturing instrument for joining two edges of biological tissue, such as blood vessels, using an arcuate suture needle which is driven and rotated by friction rollers via a cylindrical fly-wheel and plunger rod arrangement with a pneumatic or other drive source, so that the suture thread forms a continuous suture looped through the two tissue edges. U.S. Pat. No. 4,899,746 to Brunk describes a suturing apparatus in which an electric motor drives a curved needle around in a circular path of travel by means of a gear arrangement connecting to a plurality of drive rollers in supporting and driving arrangement with the needle. U.S. Pat. No. 5,308,353 to Beurrier describes a surgical suturing device in which an arcuate needle having outward projecting angled barbs positively engages and is rotated by a continuous loop drive belt.

However, such known automated suturing devices have not found wide use due to the inherent deficiencies of their design and operation, including needle slippage, inefficient transfer of drive motion to the advancement of the needle, inefficient and impractical drive mechanisms, and generally poor performance of the devices, particularly for microsurgical applications where a very small size for the device is required. Accordingly, there is a need for an improved suturing device which overcomes these deficiencies.

SUMMARY OF THE INVENTION

The stitcher device of the present invention is an automated stitching or suturing device in which a "C"-shaped arcuate suturing needle is positively driven in a circular path to suture tissues, including blood vessels. The "C"-shaped arcuate needle is held and advanced in increments by one-way clutches and by a drive plate and toggle mechanism powered via a drive shaft connected to an electric motor. The "C"-shaped needle and drive plate are flexibly positioned at the end of an elongated shaft. The stitcher is particularly adapted for use in microsurgery and/or in interior body spaces. For example, in coronary bypass surgery, the stitcher device of the present invention is able to precisely and rapidly place stitches to join grafts to coronary arteries and to seal leaks in the grafted vessels.

In general, it is an object of the present invention to provide an automated stitcher device which can be used for surgical and other applications. A further object of the invention is to provide a suturing instrument which can be used for microsurgical applications, including the suturing of blood vessels, and preferably which can be operated by a surgeon using one hand.

Additional objects and features of the invention will appear from the following description in which preferred embodiments are set forth in detail in conjunction with the accompanying drawings.

BRIEF DESCRIPTION OF THE DRAWINGS

FIG. 1 is a cut-away view of the distal portion of the stitcher.

FIG. 2 is a side view in cross-section of FIG. 1.

DESCRIPTION OF THE PREFERRED EMBODIMENT

Figure 1A:
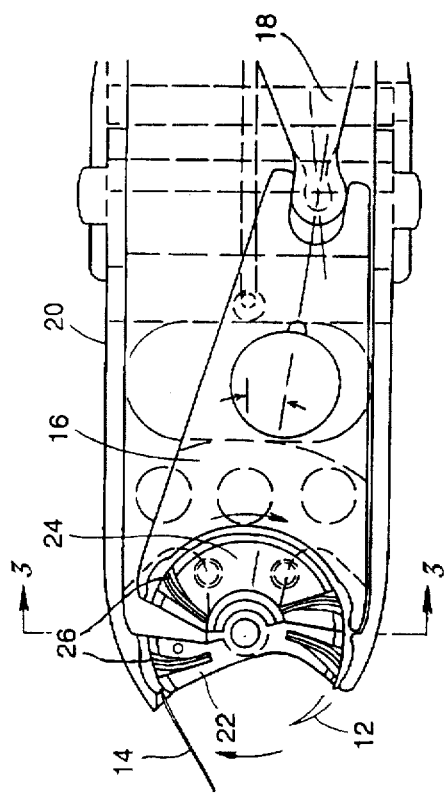
FIG. 1A is an enlarged view of the distal extremity of FIG. 1.

Turning in detail to the drawings, FIG. 1 shows the distal portion of a stitcher 10 incorporating a preferred embodiment of the present invention comprising an elongated body tube or handle 30, a head 21, and a nose tip 20 containing a "C"-shaped arcuate needle 12 with suturing thread 14 attached to the back end of the needle 12. The needle 12 is engaged and held by a static clutch body 22 and also by a dynamic clutch body 24, both of which have clutch fingers 26 which engage the inner curved surface of the needle 12 and may be composed of a stack of leaf springs. The static clutch body 22 and dynamic clutch body 24 shown in FIGS. 1 and 1A each have two clutch components, but more or less clutch components may be used for each clutch body.

Figure 4:
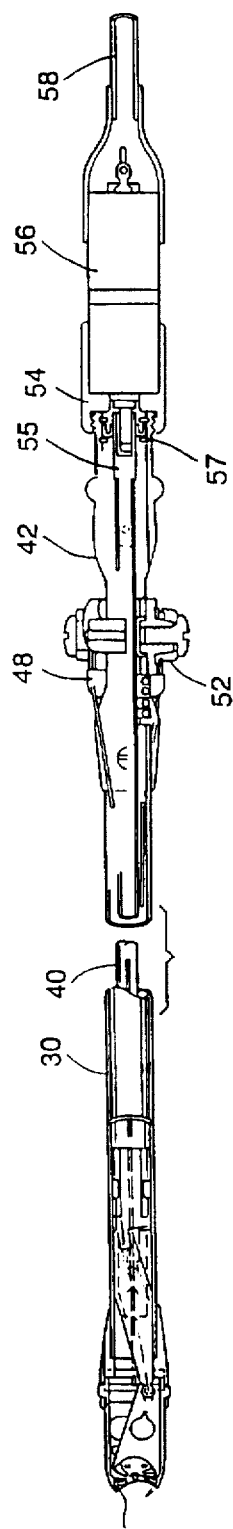
FIG. 4 is a cut-away view of the full length of the stitcher.

A crank 32 having a bearing 34, two keys 36, and thrust sleeve 38 (FIG. 5) is driven by an elongated drive tube shaft 40 which is in the preferred embodiment powered by an electric motor 56 (see FIG. 4). The crank 32 converts the rotary motion of drive shaft 40 to oscillating motion to drive needle 12.

A diamond-shaped toggle 18 pivots up and down driven by the rotation of crank 32, is shown in FIGS. 1 and 2, and toggle 18 in turn moves drive plate 16 up and down. The movement of drive plate 16 rocks the dynamic clutch body 24 back and forth, which incrementally advances the arcuate needle 12. In one embodiment, the needle is advance in 15° increments. The clutches are one-way clutches. FIG. 2 provides a side cross-sectional view of the distal portion of the stitcher 10, showing the crank 32 and its engagement with toggle 18.

Figure 3:
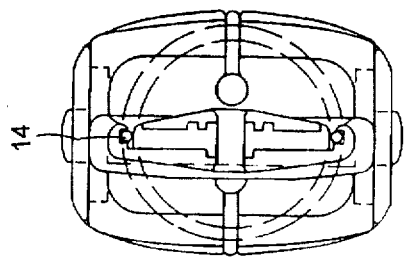
FIG. 3 is a cross-sectional end view of the distal nose tip of the stitcher.
Figure 2A:
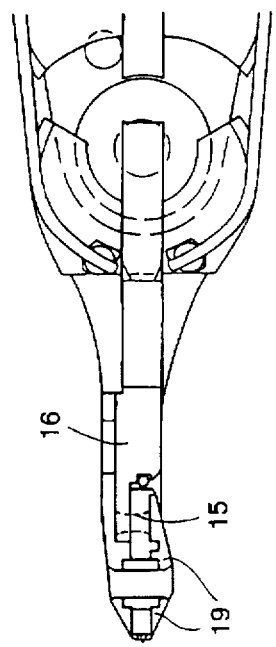
FIG. 2A is an enlarged view of the distal extremity of FIG. 2.

The forward static clutch body 22 holds the needle 12 and the flexible clutch fingers 26 permit the needle 12 to be incrementally advanced by the movement of the drive plate 16, and ensure that the needle 12 is held in place until the next incremental advancement by the drive plate 16 FIGS. 1A, 2A, and 3 show the details of the nose tip 20 at the distal extremity of the stitcher 10. FIG. 2A shows a cap plate 19 with rivet 15 of the stitcher nose tip 20. In one embodiment, the needle 12 may have corrugations on its inner curved surface for better engagement with the one-way clutch mechanism and its multiple engaging elements or clutch fingers 26. Alternately, the inner curved surface of the needle 12 may be roughened, or contain gears, ratchet teeth, or like protrusions to aid in gripping of the clutch elements.

As shown in FIG. 3, the thread 14, being attached to the back end of the needle 12 (see upper portion of FIG. 3), will follow the rotation of the needle, but may be offset from the path of the needle 12. The components of the nose tip 20 may form an arcuate guide within which the arcuate needle 12 is disposed, and may consist of a circular groove associated with cap plate 19.

Figure 5:
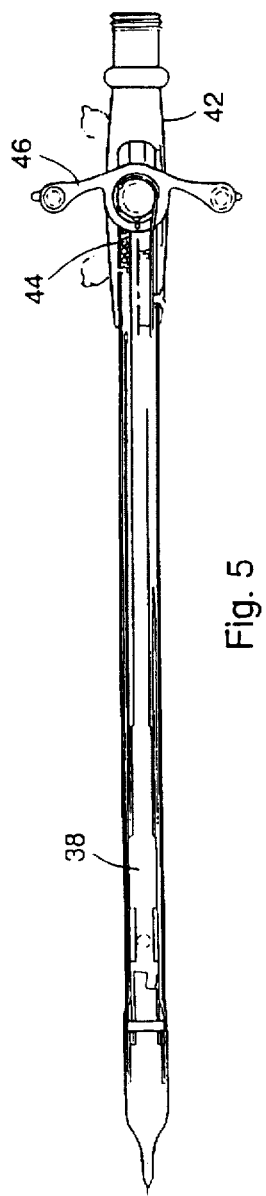
FIG. 5 is a side view of the main portion of FIG. 4.

FIG. 4 provides a view of the full length of the stitcher 10, showing a motor with gearhead 56, motor mount 54 with seal 57 and coupling 55 attached to the stitcher base 42, as well as associated electric cable 58 for the electric motor 56. FIG. 5 provides a side view of FIG. 4 up to the base portion 42. Alternately, a pneumatic, rather than an electric motor, drive could be used to provide the oscillating motion of the toggle 18 and drive plate 16.

Figure 6:
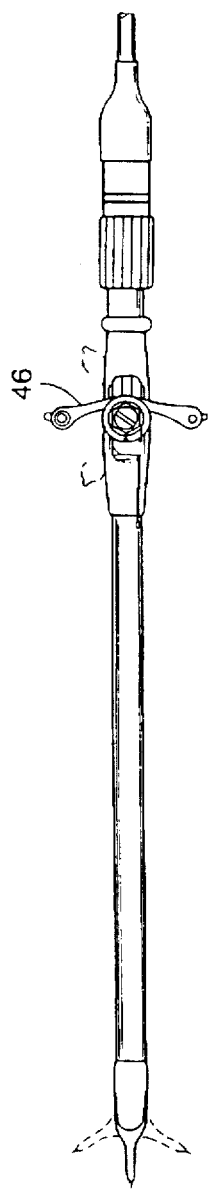
FIG. 6 is a side view of FIG. 4 showing three positions for the stitcher distal nose tip.

The nose tip 20 of the stitcher 10 is hinged to pivot at various angles, and the position of the nose tip 20 of the stitcher. 10 can be adjusted, as shown in FIG. 6, by adjusting the position of handle 46. Cable 50 (FIG. 2), with two ball fittings, provides the means to adjust the position of the nose tip 20 according to the position of the handle 46, and the position is maintained by way of cable anchor 52 and brake shoe 48. The cable anchor 52 provides the mechanism for adjusting the length of the cable, and the cable is always in tension, which can be adjusted in spring 44. As shown in FIGS. 1 and 1A, the entire nose tip 20, including the needle 12 and drive plate may be pivoted while maintaining the contact and movement between the drive plate 16 and the toggle 18. The spherical end of toggle 18 which engages drive plate 16 permits the tip to pivot and yet maintain the oscillating motion to drive the needle 12.

The way in which the "C"-shaped needle 12 is engaged or held and advanced by the drive plate 16 and toggle 18 combination as disclosed permits the stitcher 10 to have a tip whose dimensions are not much larger than the width and height of the needle 12 itself. The resulting small tip and profile of the stitcher 10 provides good site access and visibility to the surgeon. Some or all of the distal portion of the stitcher 10 may comprise a removable cartridge containing at least the needle 12 and attached thread 14 and which may be disposable.

It is contemplated that other one-way clutch mechanisms may be utilized to hold and facilitate incremental advancement of the arcuate needle 12 by the drive plate 16. For example, one-way bearings or rollers may be used, positioned along the inner curved side or the outer curved side of the arcuate needle and such bearings or roller clutches could serve to engage, hold, or secure the needle while permitting its one-way incremental advancement.

It is further contemplated that the disclosed one-way clutch mechanism may be utilized to engage, hold, and facilitate advancement of an arcuate needle by various other drive means, including drive means which provide continuous, rather than incremental, advancement of the arcuate needle.

Although the stitcher 10 of the present invention has been described principally in conjunction with surgical suturing applications, it should be appreciated that it is not limited to surgical uses, and can also be used for any sewing or stitching application. Further, while embodiments and applications of this invention have been shown and described, it would be apparent to those skilled in the art that many other and further embodiments of the invention are possible without departing from the inventive concepts herein. The invention therefore, is not to be restricted except in the spirit of the appended claims.

What is claimed is:

1. An automated stitching device having a means for incrementally advancing an arcuate needle in a circular path, wherein said means for incrementally advancing said arcuate needle comprises a drive plate means and a toggle means and further comprises a one-way clutch means, and wherein said one-way clutch means comprises at least one static clutch body means and at least one dynamic clutch body means, and wherein said one-way clutch means further comprises multiple clutch fingers.

2. An automated stitching device having a means for incrementally advancing an arcuate needle in a circular path, wherein said means for incrementally advancing said arcuate needle comprises a drive plate means and a toggle means and further comprises a one-way clutch means, said one-way clutch means further comprises multiple clutch fingers, and wherein said arcuate needle includes protuberances along its interior curved surface for engagement with said one-way clutch means.

3. An automated stitching device comprising a means for advancing an arcuate needle in a circular path and having one-way clutch means to engage and advance said arcuate needle, wherein said one-way clutch means comprises at least one static clutch body means and at least one dynamic clutch body means, and wherein said one-way clutch means further comprises multiple clutch fingers.

4. The device of claim 3 wherein said device is a surgical suturing device.

5. An automated stitching device for advancing an arcuate needle in a circular path, comprising:
 a drive plate means;
 a toggle means coupled to said drive plate means for toggling the direction of motion of said drive plate means;
 a dynamic clutch body means coupled to said drive plate means; and
 a static clutch body means associated with said drive plate means;
 wherein at least one of said dynamic clutch body means and said static clutch body means comprises multiple clutch fingers for engaging said arcuate needle, said clutch fingers configured for advancing said arcuate needle solely in one direction.

6. The device of claim 5 wherein said arcuate needle includes protuberances along an interior curved surface for engagement with said multiple clutch fingers.

* * * * *

UNITED STATES PATENT AND TRADEMARK OFFICE
CERTIFICATE OF CORRECTION

PATENT NO. : 5,709,693
DATED : January 20, 1998
INVENTOR(S) : Charles Taylor

It is certified that error appears in the above-identified patent and that said Letters Patent is hereby corrected as shown below:

On the title page, item [73], change the Assignee from "Cardiothoracic System, Inc." to --Cardiothoracic Systems, Inc.--.

Column 2, line 58, change "drive plate 16" to --drive plate 16.--.

Column 3, line 27, change "drive plate" to --drive plate 16 ,--.

Column 3, line 48, change "arcuate needle" to --arcuate needle 12 ,--.

Signed and Sealed this

Twenty-seventh Day of July, 1999

Attest:

Q. TODD DICKINSON

*Attesting Officer*     *Acting Commissioner of Patents and Trademarks*